(12) United States Patent
Warburton

(10) Patent No.: US 10,837,949 B1
(45) Date of Patent: Nov. 17, 2020

(54) PERACETIC ACID SENSOR WITH FILTER TO REMOVE HYDROGEN PEROXIDE

(71) Applicant: Piers Richard Warburton, Sewickley, PA (US)

(72) Inventor: Piers Richard Warburton, Sewickley, PA (US)

( * ) Notice: Subject to any disclaimer, the term of this patent is extended or adjusted under 35 U.S.C. 154(b) by 320 days.

(21) Appl. No.: 15/917,021

(22) Filed: Mar. 9, 2018

Related U.S. Application Data

(63) Continuation-in-part of application No. 15/069,442, filed on Mar. 14, 2016, now abandoned, which is a continuation-in-part of application No. 13/848,163, filed on Mar. 21, 2013, now abandoned.

(60) Provisional application No. 61/614,000, filed on Mar. 22, 2012.

(51) Int. Cl.
*G01N 27/04* (2006.01)
*G01N 33/00* (2006.01)

(52) U.S. Cl.
CPC ......... *G01N 33/0014* (2013.01); *G01N 27/04* (2013.01); *G01N 33/0047* (2013.01)

(58) Field of Classification Search
CPC ................................ G01N 27/04; G01N 33/00
USPC ................................ 422/90, 98; 436/129, 135
See application file for complete search history.

(56) References Cited

U.S. PATENT DOCUMENTS

| | | | | |
|---|---|---|---|---|
| 3,146,243 A | * | 8/1964 | Andersen | C07D 303/42 549/542 |
| 3,724,469 A | * | 4/1973 | Reynolds | A24D 3/16 131/334 |
| 3,912,451 A | | 10/1975 | Gaglia, Jr. | |
| 4,001,375 A | * | 1/1977 | Longo | B01D 53/8603 423/244.01 |
| 4,012,342 A | * | 3/1977 | Dougherty | C08F 10/00 521/62 |
| 4,036,942 A | * | 7/1977 | Sibeud | B01D 53/48 423/576.2 |
| 4,091,822 A | * | 5/1978 | Ihrig | A24D 3/16 131/331 |
| 4,200,609 A | * | 4/1980 | Byrd | B01D 53/8675 422/122 |
| 4,503,195 A | * | 3/1985 | Bauld | B01J 31/0239 525/333.4 |
| 4,592,905 A | * | 6/1986 | Plummer | B01D 53/52 423/226 |
| 4,622,212 A | * | 11/1986 | McManus | B01D 53/1493 252/189 |

(Continued)

FOREIGN PATENT DOCUMENTS

| | | | |
|---|---|---|---|
| DE | 3831879 | * | 3/1990 |
| JP | 3-275063 | * | 12/1991 |

OTHER PUBLICATIONS

Staritzky, E., Analytical Chemistry 1956, 28, 2022-2023.*

(Continued)

*Primary Examiner* — Arlen Soderquist

(57) ABSTRACT

A filter that is used in conjunction with a non-specific gas sensor for PAA, which allows specific detection of PAA vapor in the presence of hydrogen peroxide vapor through the removal of the hydrogen peroxide vapor. The filter contains a filter catalyst that will catalyze the disproportionation of hydrogen peroxide but not react with PAA vapor, thus removing the hydrogen peroxide vapor and allowing the peracetic vapor to pass through the filter to the sensor.

19 Claims, 3 Drawing Sheets

(56) References Cited

U.S. PATENT DOCUMENTS

| | | | | |
|---|---|---|---|---|
| 4,626,373 A | * | 12/1986 | Finch | C11D 3/3935 510/311 |
| 4,633,704 A | | 1/1987 | Tantram et al. | |
| 4,857,296 A | * | 8/1989 | Brunelle | B01D 53/8603 423/574.1 |
| 4,935,371 A | * | 6/1990 | Rickloff | A61L 2/0094 210/501 |
| 4,958,014 A | * | 9/1990 | Shirokaze | C08J 3/14 536/56 |
| 5,331,310 A | | 7/1994 | Stetter | |
| 5,395,493 A | * | 3/1995 | Pinkowski | G01N 27/4045 204/412 |
| 5,438,002 A | * | 8/1995 | Mallard de la Varende | A61L 2/18 436/129 |
| 5,451,704 A | * | 9/1995 | Ho | B01J 37/0215 502/113 |
| 5,503,720 A | * | 4/1996 | Teske | G01N 27/49 204/403.01 |
| 5,538,931 A | * | 7/1996 | Heinrichs | B01J 23/40 502/234 |
| 5,560,810 A | | 10/1996 | Constantine | |
| 5,594,115 A | * | 1/1997 | Sharma | C07K 7/06 435/69.7 |
| 5,634,880 A | * | 6/1997 | Feldman | A61B 1/00057 600/132 |
| 5,731,472 A | * | 3/1998 | Leung | C07C 45/505 568/454 |
| 5,744,697 A | * | 4/1998 | Martell | G01N 27/4045 204/412 |
| 5,841,021 A | * | 11/1998 | De Castro | G01N 27/4162 73/23.2 |
| 5,865,973 A | * | 2/1999 | Kiesele | G01N 27/404 204/412 |
| 5,879,527 A | * | 3/1999 | Kiesele | B01D 39/1661 204/276 |
| 5,942,152 A | * | 8/1999 | Tafesh | C11D 3/3932 252/186.33 |
| 5,986,152 A | * | 11/1999 | Muller | B01J 23/83 570/243 |
| 6,004,469 A | * | 12/1999 | Sanders | C02F 1/705 210/763 |
| 6,203,767 B1 | * | 3/2001 | Leasko | A61L 2/18 422/28 |
| 6,280,778 B1 | * | 8/2001 | Gaudet | A61K 36/185 424/725 |
| 6,284,545 B1 | | 9/2001 | Warburton | |
| 6,307,116 B1 | * | 10/2001 | Heinrichs | B01J 23/40 423/579 |
| 6,410,338 B1 | * | 6/2002 | Lippold | A61L 2/28 422/29 |
| 6,432,661 B1 | * | 8/2002 | Heitfeld | A01K 1/0152 435/192 |
| 6,558,529 B1 | * | 5/2003 | McVey | G01N 27/4045 134/113 |
| 7,132,083 B2 | | 11/2006 | Martin | |
| 7,306,774 B2 | * | 12/2007 | DeBerry | B01D 53/229 423/210 |
| 7,335,629 B2 | * | 2/2008 | Gentschev | A61K 8/19 510/311 |
| 7,341,618 B2 | * | 3/2008 | Bayer | B01D 39/16 502/402 |
| 7,349,760 B2 | * | 3/2008 | Wei | G01N 21/79 356/24 |
| 7,491,547 B1 | | 2/2009 | Warburton | |
| 7,988,911 B2 | * | 8/2011 | Centanni | A61L 2/206 422/120 |
| 7,988,944 B2 | * | 8/2011 | Ishiyama | B01J 31/1815 423/579 |
| 7,992,426 B2 | * | 8/2011 | Fleischer | G01N 27/4143 73/31.06 |
| 8,790,575 B1 | * | 7/2014 | Adiga | A61L 2/00 422/120 |
| 2001/0045119 A1 | * | 11/2001 | Warburton | G01N 33/0006 73/23.21 |
| 2002/0050161 A1 | * | 5/2002 | Warburton | G01N 13/00 73/23.2 |
| 2003/0010635 A1 | * | 1/2003 | Kiesele | G01N 27/404 204/415 |
| 2003/0141026 A1 | * | 7/2003 | Norborg | B65D 65/42 162/125 |
| 2003/0175983 A1 | * | 9/2003 | Wei | G01N 21/79 436/163 |
| 2004/0217049 A1 | * | 11/2004 | Bayer | B01D 39/16 210/500.36 |
| 2004/0234569 A1 | * | 11/2004 | Nakada | A61L 2/10 424/405 |
| 2005/0014948 A1 | * | 1/2005 | Galbo | C07D 211/94 546/184 |
| 2005/0042133 A1 | * | 2/2005 | Staphanos | G01N 21/77 422/50 |
| 2006/0029533 A1 | * | 2/2006 | DeBerry | B01D 53/229 423/210 |
| 2007/0114121 A1 | * | 5/2007 | Kinlen | C01B 15/01 204/175 |
| 2008/0145437 A1 | * | 6/2008 | Amundson | A61K 8/0208 424/490 |
| 2008/0219916 A1 | * | 9/2008 | Ishiyama | B01J 31/1815 423/579 |
| 2008/0293563 A1 | * | 11/2008 | Ding | B01J 21/18 502/150 |
| 2009/0062110 A1 | * | 3/2009 | Koshino | B01J 31/1815 502/159 |
| 2009/0130047 A1 | * | 5/2009 | Weiss | A61L 9/015 424/76.2 |
| 2009/0318681 A1 | * | 12/2009 | Matsunaga | B01J 31/1805 540/465 |
| 2010/0105853 A1 | * | 4/2010 | Matsunaga | B01J 31/1815 526/241 |
| 2010/0105909 A1 | * | 4/2010 | Matsunaga | B01J 31/1805 546/6 |
| 2010/0252451 A1 | * | 10/2010 | Warburton | G01N 27/404 205/779.5 |
| 2011/0286899 A1 | * | 11/2011 | Martini | B01D 46/002 423/210 |
| 2011/0294658 A1 | * | 12/2011 | Lefevre | B01J 23/745 502/185 |
| 2012/0021897 A1 | * | 1/2012 | Iwata | C07D 471/22 502/159 |
| 2013/0259743 A1 | * | 10/2013 | Keasler | C02F 1/50 422/29 |
| 2014/0072836 A1 | * | 3/2014 | Mills | C25B 1/04 429/8 |
| 2014/0099571 A1 | * | 4/2014 | Proietti | H01M 4/9041 429/527 |
| 2014/0121271 A1 | * | 5/2014 | Olson | A01N 37/16 514/557 |
| 2015/0158021 A1 | * | 6/2015 | Lee | D06M 13/355 522/137 |

OTHER PUBLICATIONS

Koubek, E. et al, Journal of the American Chemical Society 1963, 85, 2263-2268.*
Cota, H. M. et al, Nature 1964, 203, 1281.*
Walling, C., Inorganic Chemistry 1970, 9, 931937.*
Walling, C., Accounts of Chemical Research 1975, 8, 125-131.*
Francis, K. C. et al, Journal of the Chemical Society Dalton Transactions 1985, 493-501.*
Dasgupta, P. K. et al, Analytical Chemistry 1985, 57, 1009-1012.*
Balasubramanian, P. N. et al, Proceedings of the National Academy of Sciences USA 1987, 84, 1734-1738.*
Gokak, D. T. et al, Journal of Applied Polymer Science 1988, 35, 1523-1535.*
Eberhardt, M. K. et al, Biochimica et Biophysica Acta 1993, 1157, 102-106.*

(56) References Cited

OTHER PUBLICATIONS

Pokol, G. ert al, JOurnal of Thermal Analysis 1994, 42, 343-359.*
Bensalem, A. et al, Applied Catalysis A: General 1995, 121, 81-93.*
Patra, A. et al, Journal of Sol-Gel Science and Technology 1997, 9, 65-69.*
Neimeier, R. et al, Chemical Engineering & Technology 1997, 20, 391-395.*
Harms, D. et al, Analyst, 1998, 123, 2323-2327.*
Tachiev, G. et al, International Journal of Chemical Kinetics 2000, 32, 24-35.*
Christensen, C. S. et al, Journal of Environmental Monitoring 2000, 2, 339-343.*
Hwu, J. R. et al, Journal of Organic Chemistry 2000, 65, 5077-5088.*
Wang, C.-C. et al, Journal of Applied Polymer Science 2001, 82, 3248-3257.*
Khalil, L. B. et al, Journal of Chemical Technology and Biotechnology 2001,76, 1132-1140.*
Ishtchenko, V. V. et al, Applied Catalysis A: General 2003, 242, 123-137.*
Hecht, G. et al, Annals of Occupational Hygiene 2004, 48, 715-721.*
Kiseleva, E. N. et al, Russiona Journal of General Chemistry 2007, 77, 641-647.*
Sung, W. et al, Journal of Power Sciences 2007, 172, 198-208.*
Gabelica, Z. et al, Journal of Thermal Analysis and Calorimetry 2009, 95, 445-454.*
Zhang, L. et al, Sensors and Actuators B 2014, 193, 752-758.*
Sigel, H. et al, Journal of the American Chemical Society 1969, 91, 1061-1064.*
Hendriks, C. F. et al, Industrial & Engineering Chemistry Product Research and Development 1979, 18, 38-43.*
Sigel, H. et al, Inorganic Chemistry 1979, 18, 1354-1358.*
Banerjee, P. et al, Bulletin of the Chemical Society of Japan 1981, 64, 2496-2498.*
Mochida, I. et al, Journal of Physical Chemistry 1982, 86, 3468-3471.*
Oishi, N. et al, Polyhedron 1984, 3, 157-160.*
El-Sheikh, M. Y. et al, Journal of Molecular Catalysis 1989, 55, 396-405.*
Shivanekar, A. et al, Transition Metal Chemistry 1990, 15, 226-230.*
Gemeay, A. H., Colloids and Surfaces A: Physicochemical and Engineering Aspects 1996, 116, 277-284.*
Gemeay, A. H.et al, Colloids and Surfaces A: Physicochemical and Engineering Aspects 1996, 117, 245-252.*
Deshmukh, A. P. et al, Journal of Molecular Catalysis A: Chemical 2000, 153, 75-82.*
Hanaoka, S. et al, Analytica Chimica Acta 2001, 426, 57-64.*
Jäkärä, J. et al, in "Oxidative Delignification Chemistry", ACS Symposium Series 2001, vol. 785, Chapter 10, 182-196.*
Awad, M. I. et al, Analytical Chemistry 2003, 75, 2688-2693.*
Pettas, I. A. et al, Analytica Chimica Acta 2004, 522, 275-280.*
Popov, E. et al, Holzforschung 2005, 59, 507-513.*
Li, J. et al, Electrochimica Acta 2011, 56, 3159-3163.*
Hua, M.-Y. et al, Electrochimica Acta 2011, 56, 4618-4623.*
Awad, M. I., Analytica Chimica Acta 2012, 730, 60-65.*

* cited by examiner

PERACETIC ACID SENSOR WITH FILTER TO REMOVE HYDROGEN PEROXIDE

PRIORITY

This application is a continuation in part of U.S. application Ser. No. 15/069,442 fled on 2016 Mar. 14, now abandoned, which was a continuation in part of U.S. application Ser. No. 13/848,163, filed on 2013 Mar. 21, now abandoned; which claims the benefit of U.S. Provisional Application No. 61/614,000, filed on 2012 Mar. 22.

FIELD OF THE INVENTION

The field of this invention is filters used to improve the selectivity of gas sensors.

BACKGROUND OF THE INVENTION

Toxic gases and vapors are found in many workplace environments and employers have a legal duty to ensure that the work place is safe for employees [Sec. 5, Occupational Safety and Health Act of 1970]. The American Conference of Governmental and Industrial Hygienists (ACGIH) has developed threshold limit values (TLVs) for many gases and vapors, below which the gas or vapor concentration is believed to be safe for the majority of workers [2014 Threshold Limit Values for Chemical Substances and Physical Agents & Biological Exposure Indices, Publ. ACGIH]. The Occupational Safety and Health Administration (OSIA) has promulgated permissible exposure limits (PELs) for many gases and vapors in 29 CFR 1910.1000 Table Z-1, which limit the maximum exposure of workers to toxic gases and vapors allowed by law.

In chemical terminology, a gas is a molecule (including mono-atomic gases) in the gas phase at a temperature above its boiling points and a vapor is a molecule in the gas phase at a temperature below its melting point. However, in the present disclosure the term vapor is also used to refer to peracetic acid (PAA) or hydrogen peroxide molecules as a small component of a gas mixture, and the term gas is used to refer to the bulk gas. For example, a test gas may comprise a low concentration of PAA vapor in a balance of air or the air sample may contain hydrogen peroxide vapor.

To enable employers to meet these exposure limits, various chemical means have been developed to measure the concentration of the target vapor. These means include drawing an air sample through a solution or reagent filled impinger and performing a chemical analysis, collecting the sample in a charcoal tube for later analysis, gas/vapor exposure badges wherein a collecting chemical reagent is impregnated into a badge that is exposed to the work place atmosphere and later sent off for analysis. In recent decades electronic monitors have been developed for many gases and vapors that provide a real time reading of the gas/vapor concentration and often include automatic triggering of alarms if the gas or vapor concentration exceeds threshold limits, as well as data collection and storage and other functions available with modern electronics.

These monitors typically consist of a sensor that provides an electronic output that varies with the gas/vapor concentration, electronics to drive the sensor and amplify the signal, signal processing to convert the signal into a usable number and audible and visual displays to inform and if necessary alert the user if the gas/vapor concentration is above preset limits. Many types of sensor are known in the prior art including sensors based on electrochemical, infrared, photoionization, photoacoustic and metal oxide semiconductor technologies.

PAA, also known as peroxyacetic acid ($CH_3C(O)O_2H$), forms an equilibrium mixture with hydrogen peroxide and acetic acid such that it is formed in solution if acetic acid and hydrogen peroxide are mixed together. PAA is almost always used in a mixture with hydrogen peroxide and acetic acid.

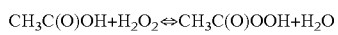

$$CH_3C(O)OH + H_2O_2 \Leftrightarrow CH_3C(O)OOH + H_2O$$

Wherever PAA solution is used, there will be some PAA vapor present in the gas phase and conversely, wherever there is PAA vapor present, there will also be some hydrogen peroxide vapor present as well.

In addition to use with PAA solution, hydrogen peroxide solution is often used as a disinfectant solution; and it is widely used as a steriliant gas to sterilize medical equipment and similarly as a biocide in the food industry. Often the hydrogen peroxide is used on the same or nearby equipment as PAA and so there is a significant risk of exposure of the PAA sensor to hydrogen peroxide vapor, either from evaporation of hydrogen peroxide from the PAA solution or from nearby equipment.

Most disinfectants and sterilants are designed to destroy a wide range of biological organisms and so these compounds are usually toxic to humans and thus exposure to these chemicals in the workplace is potentially hazardous. OSHA has promulgated PELs for many common sterilants and disinfectants that have significant vapor pressure.

Hydrogen peroxide is a strong oxidizing agent, the standard potential for the half cell reaction:

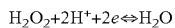

$$H_2O_2 + 2H^+ + 2e \Leftrightarrow H_2O$$

E=1.776V vs. SHE ["CRC Handbook of Chemistry and Physics", 76$^{th}$ Ed, 1995-1996, D. R. Lide Ed in Chief; CRC Press Boca Raton, SHE=standard hydrogen electrode]. The strongly oxidizing properties of hydrogen peroxide make its vapor very hazardous and consequently the Occupational Safety and Health Administration (OSHA) has set a permissible exposure limit (PEL) for hydrogen peroxide of 1 ppm calculated as an eight-hour time weighted average [29 CFR 1910.1000, Table Z-1]. PAA is a stronger oxidizing agent than hydrogen peroxide (E=1.98 V vs. SHE), [calc. from data in M. I. Awad, et al. J. Electrochemical Soc. (2004), 151(12), E358-363 (Abstract)] and even though there is no OSHA PEL for PAA, PAA may be expected to be more hazardous than hydrogen peroxide.

PAA is approved as a sanitizer for food use by the US Food and Drug Administration (FDA) [21 CFR 178.1010 (25, 30)] and for use as a high level disinfectant of sterilant for reusable medical and dental devices [FDA-Cleared Sterilants and High Level Disinfectants with General Claims for Processing Reusable Medical and Dental Devices—March 2015, available at http://www.tda.gov/MedicalDevices/DeviceRegulationandGuidance/ReomcessingofReusableMedicalDevices/ucm437347.htm, retrieved Mar. 7, 2018] and is widely used in both healthcare and the food processing industry. There many reports of workers experiencing irritation to eyes and respiratory system; and exposure limits for PAA have been suggested (e.g. 0.2 ppm as an 8 hr TWA, [F. Gagnaire, B. Marignac, G. Hecht, M. Hery, "Sensory Irritation of Acetic Acid, Hydrogen Peroxide, Peroxyacetic acid and their Mixture in Mice," Annals of Occupational Hygiene, (2002), 46(1), 97-1021). The US Environmental Protection Agency (EPA) has developed Acute Exposure Guidelines Levels (AEGLs) for PAA equal to 0.17, 0.52 and 1.3 ppm for AEGLs 1, 2 and 3, calculated as 10 minute to 8 hour time weighted averages. [Health Risks of PAA, https://www.epa.gov/aegl/peracetic-acid-results-aegl-program, retrieved Mar. 7, 2018], AEGLs 1 to 3 estimate the exposure levels corresponding to transient irritation, severe irritation and risk of injury, to life threatening health effects respectively. More detailed definitions are available [AEGL.Definitions https://www.epa.gov/aegl/about-acute-exposure-guideline-levels-aegls#assigned, retrieved Mar. 7, 2018]. In 2014 the ACGIH issued a short-term exposure limit (STEL) TLV of 0.4 ppm, calculated as a 15 minutes TWA [2014 Guide to Occupational Exposure Values, ACGIH].

Inmost applications of PAA, an aqueous solution of acetic acid, hydrogen peroxide and PAA is applied to the surface or material to be treated. All three compounds have a significant vapor pressure at room temperature and so a solution of PAA will produce significant amounts of acetic acid vapor (OSHA PEL=10 ppm [29 CFR 1910.1000 Tbl. Z-1]) and hydrogen peroxide vapor (OSHA PEL=1 ppm) as well as PAA vapor. The airborne concentrations of PAA vapor produced depend on many factors including the temperature, solution concentrations, solution application (e.g. spray versus dip tank) and air exchanges in the surrounding area.

The goal for workplace safety gas monitoring is to warn workers if the concentration of hazardous gases exceeds safe thresholds so that the workers can take preventative measures before they receive an excessive exposure to a toxic gas or vapor. A continuous monitor, using an electrochemical sensor for PAA, is commercially available from ChemDAQ Inc (Pittsburgh, Pa.), which provides a continuous reading of the concentration of PAA in ambient air. This PAA monitor is able to detect PAA over a range of 0 to 3 ppm, with a minimum detection limit of 0.04 ppm and a digital resolution of 0.01 ppm.

The sensors used in the monitor respond to PAA vapor well but have a cross sensitivity to hydrogen peroxide vapor. Thus, the signal to PAA is increased or decreased in the presence of hydrogen peroxide depending on the sensor used. This cross sensitivity produces an apparently higher or lower concentration of PAA than would be measured in the absence of the hydrogen peroxide vapor. Since PAA is formed, and is almost always used, as an equilibrium mixture with hydrogen peroxide and acetic acid, there will always be some hydrogen peroxide vapor present. Some commercial formulations of PAA even have a higher concentration of hydrogen peroxide than PAA and thus the cross sensitivity can be very significant.

What is needed is a method to reduce the cross sensitivity to hydrogen peroxide. The use of chemical filters within sensors is well known in the prior art; for example, Tantram and Chan in U.S. Pat. No. 4,633,704 describe the use of a soda lime filter to prevent hydrogen sulfide from giving a response on a carbon monoxide sensor; Warburton and Sawtelle described a filter based on silver salts also to eliminate cross sensitivity of a chlorine dioxide sensor to hydrogen sulfide in U.S. Pat. No. 6,284,545 and Warburton described a filter to remove alcohols and carbon monoxide for use with an ethylene oxide sensor (Warburton, U.S. Pat. No. 7,491,547). Filters are placed in the gas path such that all the gas that reaches the sensor must pass through the filter. The filter is designed to remove the interferent gas but not the target gas. However chemical filters cannot be used for all types of gas sensors being limited by the available chemistry to differentiate between the target and interferent gases.

SUMMARY OF THE INVENTION

It is therefore an object of the present invention to provide a filter for use with PAA sensors for removal of hydrogen peroxide vapor without adversely affecting the response of the sensor to PAA. A chemical filter has been developed that is placed in the gas path to a PAA sensor. This filter will allow low concentrations of PAA to pass through, but will chemically react with hydrogen peroxide vapor, removing it from the gas stream and so preventing it from reaching the sensor. This filter is sufficiently compact that it can be incorporated within a gas detection monitor containing the sensor enabling the cross sensitivity of the sensor to hydrogen peroxide will be greatly reduced.

BRIEF DESCRIPTIONS OF THE DRAWINGS

DETAILED DESCRIPTION OF THE INVENTION

Figure 1:
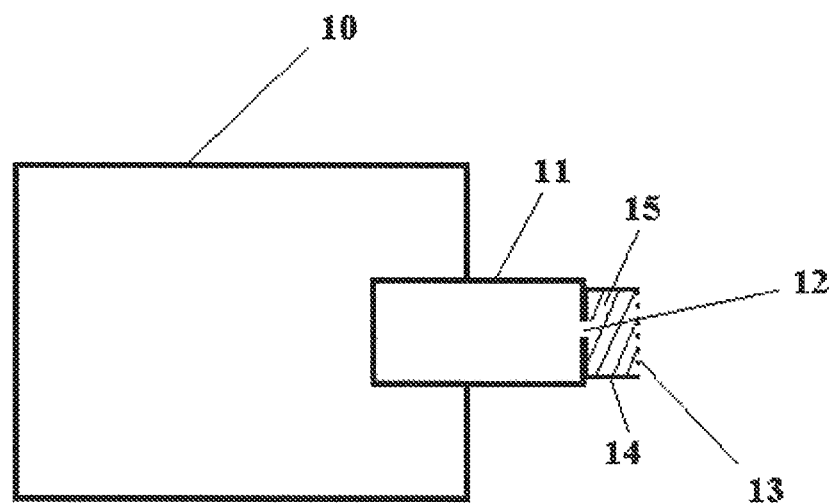
FIG. 1 is a cross-sectional diagram of a gas detection apparatus showing a filter operating in a diffusion mode.

The role of a chemical filter for a gas sensor is to allow the target gas to pass through the filter but prevent unwanted gases that would otherwise give a response on the sensor from reaching the sensor. For PAA sensors, the main interfering vapor is hydrogen peroxide. Therefore, a chemical filter for a PAA sensor must allow essentially all of the PAA vapor to pass through freely but prevent essentially all of the hydrogen peroxide vapor from reaching the sensor. In practice, some of the PAA will be absorbed or otherwise removed by the filter. This reduction in signal can be compensated by adjusting the sensor calibration but if too much of the PAA is removed the signal to noise ratio from the sensor will decrease to an unacceptable level. For the sensors that were used in the testing in this application, which are primarily used for occupational safety applications, essentially all of the PAA passing through means at least 60% of the PAA passes through the filter. Therefore, if the sensor is exposed to 1 ppm of PAA, it will respond as through exposed to at least 0.6 ppm. For other sensors, or for different applications, the ratio may be different. For workplace safety applications, the filter needs to prevent essentially all of the hydrogen peroxide vapor from reaching the sensor, otherwise it may give a cross sensitivity. The minimum efficiency that meets the essentially all requirement is about 90%, i.e. if 10 ppm hydrogen peroxide is applied to the sensor, less than or equal to 1 ppm will reach the sensor otherwise the cross sensitivity response to hydrogen peroxide will be problematic.

Most sensors for PAA vapor are electrochemical sensors, comprised of a two or three electrode cell with an outer membrane through which the PAA enters by diffusion to reach the working electrode. At the working electrode, the PAA is reduced to acetic acid and the resulting electrical current is proportional to the PAA concentration. These sensors are either designed to work in diffusion mode, i.e. the sensor detects PAA in the air near the sensor that diffuses into the sensor. Alternatively, the air may be drawn from a remote location by a pump and passed over the sensor (so-called sample draw), and the PAA diffuses into the sensor and is reduced at the working electrode. In both cases, the limiting step is diffusion of the PAA vapor into the sensor. If the filter is placed in front of the sensor, in diffusion sampling mode, the PAA now has to diffuse through the filter and then into the sensor. If the sample draw method is used, then the PAA filter is either placed in the gas line and the PAA passes through the filter with the test gas flow, or immediately in front of the sensor, so that the PAA enters the sensor by diffusion. The design of this filter for either of these applications is well known in the art, and same considerations are involved for any other chemical specific filter used with gas sensors. Examples of prior art chemical filters for gas sensors that employ these design considerations include U.S. Pat. Nos. 7,491,547, 6,284,545 and 5,560,810. Sometimes the filter is placed between the outer membrane and the inner electrode membrane, for example U.S. Pat. No. 4,633,704. In all of these filters, the filter has to allow unhindered passage of the target gas or vapor and remove essentially all of the interfering gas or vapor.

The theories outlined herein are presented for information purposes and represent the inventor's best understanding of the operation of the filter but the disclosure of the theories presented is not intended to provide any limitation on the scope of the invention.

A chemical filter can be a pure substance, but most commonly a filter is an inert support material with an active agent deposited on it. The active agent must react with the interfering compounds and not react with the target gas. A compound is therefore needed that will react with hydrogen peroxide but not PAA. There are several compounds that react with hydrogen peroxide but not PAA in the prior art.

For example, PAA and hydrogen peroxide can be analytically determined in solution by iodometic titration to measure the combination of hydrogen peroxide and PAA and potassium permanganate titration to measure just the hydrogen peroxide. [Bodiroga M. Ognjanović J.; "Determination of PAA and hydrogen peroxide in a preparation" *Vojnosanit Pregl.* 2002 May-June; 59(3):277-9; Abstract available from http://www.cbi.nlm.nih.gov/pubmed/12132242, retrieved Mar. 7, 20181]. A similar system has been developed using cerium(IV) sulfate instead of potassium permanganate [Hydrogen Peroxide, Peroxyacetic Acid, Octanoic Acid, Peroxyoctanoic Acid, and 1-Hydroxyethylidene-1,1-Diphosphonic Acid (Hedp) as Components of Antimicrobial Washing Solution Chemical and Technical Assessment (CTA); Ma. Patricia V. Azanza, 2004; for the Joint FAO/WHO Expert Committee on Food Additives (administered jointly by the Food and Agriculture Organization of the United Nations and the World Health Organization). Available from http://www.fao.org/fileadmin/templates/agns/pdf/iecfa/cta/63/Antimicrobials.pdf, retrieved Mar. 7, 2018].

Another system for analyzing hydrogen peroxide and PAA vapors consists of an absorption medium consisting of quartz fiber filters impregnated with titanium oxysulfate hydrate for the sampling of hydrogen peroxide followed by; a tube filled with silica gel soaked with methyl p-tolylsulfoxide for the sampling of PAA. The absorbed components then being determined by subsequent desorption of the analytes by laboratory methods [Simultaneous Sampling of Peroxyacetic Acid and Hydrogen Peroxide in Workplace Atmospheres; G. Hecht, M. Héry, G. Hubert And I. Subra; *The Annals of Occupational Hygiene* (2004). Volume 48, Issue 8, pp 715-721].

All of the above chemistries use a chemical reagent that reacts with the hydrogen peroxide and thus the reagent is consumed in the filtering process. This consumption means that the filter must contain enough of the reactive component to react with all the hydrogen peroxide that the sensor will be exposed to over the expected service life of the filter. Such filters therefore, tend to be large or require frequent replacement. For diffusion limited sensors, a larger filter also tends to present a larger diffusion barrier and thus lowers the sensitivity of the sensor.

The present invention employs a hydrogen peroxide disproportionation catalyst, rather than a reagent and so does not suffer from the above limitations. Disproportionation catalysts are compounds that catalyze the disproportionation of hydrogen peroxide to oxygen and water because hydrogen peroxide has both oxidative and reducing properties. During the disproportionation reaction the hydrogen peroxide is oxidized to produce oxygen and reduced to produce water.

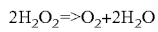

$$2H_2O_2 => O_2 + 2H_2O$$

Hydrogen disproportionation catalysts have been known since the nineteenth century and have been well studied and include iron, manganese, copper and silver compounds [J. W. Mellor, "A Comprehensive Treatise on Inorganic and Theoretical chemistry, vol. 1 H, O" Longmans, Green & Co. Ltd, London (1927), 936-949]

PAA is a strong oxidizing agent and will rarely be found to disproportionate. A few compounds though have been reported to catalyze this reaction, e.g. a bis(iron (III)(oxo) tetra(phenanthroline) complex. ["Chemo-Enzymatic Routes to Enantiopure Halohydrogen peroxides and Epoxides"; Robert M. Haak Ph.D. Thesis, Stratingh Institute for Chemistry, University of Groningen, the Netherlands (1979). Available at http://dissertations.ub.rug.nl/FILES/faculties/science/2008/r.m.hacetic_acidk/c2.pdf, retrieved Mar. 20, 2012] and various vanadium complexes [Mechanism of combined decomposition of hydrogen peroxide and PAA catalyzed by vanadium complexes. P. Makarov, A. E. Gekhman, O. Ya. Polotnyuk and I. I. Moiseev, *Russian Chemical Bulletin*, Volume 34, Number 4, 694-696, abstract available http://www.springerlink.com/content/vlm4126511203146/, retrieved Mar. 7, 2018].

Even though disproportionation of PAA is rare, PAA is such a strong oxidizing agent that it will react with many transition metal compounds, even those in high oxidation states forming reactive intermediates and several transition metal complexes have been used as epoxidation catalysts in the reaction of PAA with organic substrates. For example, the μ-oxo-iron(III) dimer, [((phen)$_2$(H$_2$O)FeIII)$_2$(μ-O)](ClO$_4$)$_4$, is an efficient epoxidation catalyst for a wide range of alkenes, including terminal alkenes, using PAA as the oxidant. ["Simple Iron Catalyst for Terminal Alkene Epoxidation"; G. Dubois, A. Murphy, and T. D. P. Stack; *Org. Lett.*, 2003, 5 (14), pp 2469-2472. http://pubs.acs.org/doi/abs/10.1021/ol0347085, retrieved Mar. 7, 2018]; the reaction of naphthalene and methylnaphthalenes with PAA catalyzed by Mn(III) (1) or Fe(II) (2) octanitrophthalocyanines in CH$_3$CN at 20° C. produces 1,4-naphthoquinones [S. V. Barkanova, V. M. Derkacheva, O. V. Dolotova, V. D. Li, V. M. Negrimovsky, O. L. Kaliya, E. A. Luk'yanets; "Homogeneous oxidation of aromatics in nucleus with PAA catalyzed by iron and manganese phthalocyanine complexes" *Tetrahedron Letters*; Volume 37, Issue 10, 4 Mar. 1996, Pages 1637-1640. Available from http://www.sciencedirect.comscience/article/pii/0040403996000792, retrieved Mar. 7, 2012]and the catalytic oxygenation of alkanes by peroxyacetic acid by dinuclear manganese complex [LMn(IV)(O)$_3$Mn(IV)L](PF$_6$)$_2$, where L is 1,4,7-trimethyl-1,4,7-triazacyclononane, to give alkanols, alkanones and alkyl hydroperoxides. [J. R. Lindsay Smith, G. B. Shupin, "Efficient stereoselective oxygenation of alkanes by peroxyacetic acid or hydrogen peroxide and acetic acid catalyzed by a manganese(IV)1,4,7-trimethyl-1,4,7-triazacyclononane complex," *Tetrahedron Letters*; (1998), 39(27), 4909-4912; http://www.scienedirect.com/science/article/pii/ S0040403998008934, retrieved August 2012].

It is found that most simple inorganic compounds, especially those involving transition metals in low oxidation states, that will remove hydrogen peroxide will also remove PAA vapor. Even though the chemical literature is sparse regarding the reactions of PAA, it is thought that the removal of PAA is due to either reduction of the PAA to acetic acid, or if no reducing agent is present, then adsorption of the PAA.

However, out of solution, on the time scales required for a gas to pass through a sensor filter by diffusion, adsorption appears to be the main loss mechanism for PAA. The response time of an electrochemical sensor under diffusion control is typically about 5 to 10 seconds ["Amperometric Gas Sensor Response Times", P. Richard Warburton, Marcus P. Pagano, Robert Hoover, Michael Logman, and Kurtis Crytzer, Yi Jin Warburton, *Anal. Chem.*, 1998, 70 (5), pp 998-1006].

Several criteria have been identified as necessary to select a good material for a filter to remove hydrogen peroxide vapor from the gas path to a PAA sensor. These are described below.

The first requirement is that the compound must be stable, which for the purposes of this specification means that it must be stable over time (months to years) in the presence of both ambient air and high and low humidity. In addition, the compounds must be low cost, readily available and low vapor pressure if they are to be amenable for use in a chemical filter. It is preferable, but not essential, if the complexes are water soluble, since it facilitates deposition of the catalyst on a solid support for fabrication of the filters. It is also preferably that they be non-corrosive with low toxicity to facilitate the manufacture and use of the filters.

It is relatively easy to screen candidate compounds against the above criteria to select only the most likely candidates. Most of the necessary information is in standard chemistry references such as the CRC Handbook of Chemistry and Physics (any edition), chemical catalogs (for example the 2012-2014 Handbook of Fine Chemicals from the Sigma-Aldrich Corporation, St. Louis, Mo.) and of course the internet. Most compounds which have the necessary stability to air and humidity are well known, easily prepared and can often be purchased directly from chemical suppliers with minimal preparative work needed to prepare the catalyst compound.

It is an advantage if the filter compound is soluble in a commonly available solvent, especially water, since it makes preparation of the supported catalyst simpler. A solution of the catalyst is prepared in the solvent, some of this solution is applied to support, and the solvent is evaporated to leave the catalyst on the support.

To find a suitable active agent for a chemical filter for a PAA sensor to remove hydrogen peroxide vapor, a compound must be found that catalyzes the disproportionation of hydrogen peroxide. Many transition metal complexes are known to be able to catalyze the disproportionation of hydrogen peroxide.

Whether a complex will catalyze hydrogen peroxide is reasonably well understood in the prior art, the primary factor is the complex's redox potential. The standard potential for the reduction of oxygen to form hydrogen peroxide:

$$O_2+2H^++2e\Leftrightarrow H_2O_2$$

is 0.695V vs SHE (CRC Handbook of Chemistry and Physics, 76$^{th}$ Ed, 1995-1996) and the standard potential for the reduction of hydrogen peroxide to water:

$$H_2O_2+2H^++2e\Leftrightarrow 2H_2O$$

is 1.78 V vs. SHE (CRC Handbook of Chemistry and Physics, David R. Lide Editor in Chief, 76$^{th}$ Edition, 1995-1996) is 1.776 V vs SHE. These are standard potentials and the actual potentials in a given solution will depend on the pH of the solutions, concentration of reactants and temperature. The redox potential at any pH, concentration or temperature can be found using the well-known Nernst Equation. [https://en.wikipedia.org/wiki/Nernst_equation, accessed Mar. 8, 2018]

To catalyze the disproportionation of hydrogen peroxide, the catalyst must have at least two oxidation states with a redox potential between the two hydrogen peroxide potentials. There are many examples of hydrogen peroxide disproportionation catalysts in the prior art, for example U.S. Pat. No. 7,988,944 abstract, U.S. Pat. No. 5,711,146 abstract, U.S. Pat. No. 4,981,662 abstract, and U.S. Pat. No. 3,363,982.

The redox potentials for many metal compounds are known and many have been tabulated ("The Oxidation States of the Elements and Their Potentials in Aqueous Solution" W. M. Latimer, Prentice-Hall Inc, (1952); "Standard Potentials in Aqueous Solution", A. J. Bard, R. Parsons, J. Jordan, IUPAC, Marcel Decker Inc, (1985); "CRC Handbook of Chemistry and Physics", 76$^{th}$ Ed, 1995-96; "Atlas of Electrochemical Equilibria in Aqueous Solution", M. Pourbaix, NACE (1974)).

The redox potentials of metal complexes may also depend on the pH of the solutions, if there is one or more protons in the redox reaction, or if the complex is in equilibrium with another species involving a proton. For example, if there is a metal (M) bound to a ligand L. and the ligand is in equilibrium with the protonated form of the ligand (LH), $$M^{n+}+L\Leftrightarrow ML^{n+}, \text{ such that } K_t=[ML^{n+}]/([Mn^{n+}][L])$$

and $$L+H^+\Leftrightarrow LH^+, \text{ such that } K_a=[LH^+/([L][H^+])$$

then the pH will affect the redox potential of the metal complex as described the Nernst Equation (https://en.wikipedia.org/wiki/Nernst_equation, accessed Mar. 8, 2018] combined with the above equilibrium equations, as is well known by practitioners of the art of chemistry.

For those compounds whose redox potential have not been tabulated, the electrochemical properties of materials is one of the commonly described properties in the chemical literature, especially for transition metal complexes.

The equilibrium binding constants for the formation of many metal complexes and ligands have been tabulated, see for example, the multi-volume series "Critical Stability Constants, by A. E. Martell, R. M. Smith, Plenum Press (1974). Binding constants are thermodynamic values and the redox potential of the metal complex can be calculated from the binding constants and the standard potential of the bare metal ion. Therefore, it is relatively straight forward to determine if a candidate compound is stable in air and humidity and whether it has the appropriate redox potentials to disproportionate hydrogen peroxide.

The rate of the disproportionation reaction depends on both the potential, steric hindrance from the ligands and whether there are accessible reaction sites within the coordination sphere around the metal atoms. The disproportionation reaction of hydrogen peroxide is usually much faster via an inner sphere process and so the metal catalyst should have an available coordination site, or if all the coordination sites are occupied, then the ligands must be sufficiently labile for hydrogen peroxide to reach the metal. Whether a metal complex has a vacant coordination or labile coordination site can usually be judge by its stoichiometry. The degree to which metal complexes have labile ligands has been extensively studied and the principles behind whether a ligand is labile or not is well known by inorganic chemists (for example, "Advanced Inorganic Chemistry" by F. A. Cotton and G. Wilkinson, Jon Wiley & sons, $5^{th}$ Ed, (1988), chapter 29 "Reaction Mechanisms of Transition Metal Complexes"). Candidate compounds should therefore be chosen such that they have a vacant or labile coordination site. In testing, compounds such as potassium ferricyanide, which has no vacant coordination sites gave no reaction to either hydrogen peroxide or PAA consistent with its fully occupied coordination shell preventing binding of hydrogen peroxide.

To prevent reaction of the metal complex with PAA, the metal must be in its highest oxidation state that is stable in ambient environments, as defined above, and additionally not have another accessible higher oxidation state (stable or not) within the oxidative power of PAA. For example, some iron (III) compounds will react with peroxy compounds to produce unstable transient iron (IV) species that then further react to form stable iron (III) species again. The electrode potential for PAA is E=1.98 V vs. SHE, [calc. from data in M. I. Awad, et al. *J. Electrochemical Soc.* (2004), 151(12), E358-363 (Abstract)], and so the complex must not have a higher oxidation state with a reduction potential below about 2.0V vs. SHE. Thus the redox potential of the metal can be used to screen against potential reaction with PAA and as discussed above, the redox potential for many metal complexes is readily available in the chemical literature.

The highest available oxidation state of most metals is readily available in inorganic text books. For example, "Advanced Inorganic Chemistry" by F. A. Cotton and G. Wilkinson, Jon Wiley & sons, $5^{th}$ Ed, (1988), and later editions, provide an excellent survey of the chemistry of all the elements, including their oxidation states.

The potential of the PAA reaction will depend on the pH since the reduction of PAA involves protons in the half cell reaction:

$$CH_3C(O)OOH + 2H^+ + 2e \Leftrightarrow CH_3C(O)OH + H_2O$$

The redox potential at any pH, concentration or temperature can be found using the well-known Nernst Equation. [https://en.wikipedia.org/wiki/Nernst_equation, accessed Mar. 8, 2018].

It is not just the metal in the metal complex that can potentially be oxidized. The ligands must be stable to oxidation too. The term ligand is intended to include chelates, macrocycles and other moieties that will bind to a metal. Ligands designed for stability in highly oxidizing environments are well known in the prior art, for example U.S. Pat. No. 5,786,496. The effect of ligand/chelate/macrocycle substituents on the redox potential and stability to high oxidation states have been extensively reported in the prior art, for example U.S. Pat. No. 5,428,180. Thus, selecting an oxidatively stable ligand is well understood in the prior art.

For those complexes which are ionic, the counter ions may play little role in the chemistry, however, the counter ion should be chosen to be unreactive towards PAA. Suitable examples include acetate, nitrate, sulfate, tetrafluoroborate and hexafluorophosphate for anions and sodium, potassium, other alkali and alkaline earth metals for cations. In the listed filter catalysts herein, the counter ions have been left out because they contribute minimally to the function. Thus, there will be little difference in function between a sodium salt of an anionic metal complex and the corresponding potassium salt. The primary differences that will be observed will solubilities in water and other solvents that may affect fabrication of the filters. However, selecting appropriate counter ions is well understood by chemists and other people familiar with the art of chemistry.

Counter ions that can be oxidized by PAA, such as chloride, bromide, nitrite, sulfide, sulfite, should be avoided. For example, in our testing, a filter containing iron (III) chloride filter gave erratic results with PAA. Chloride ion has a redox potential:

$$Cl_2 + 2e \Leftrightarrow Cl^-$$

E=1.36 V vs SHE (CRC Handbook of Chemistry and Physics) lower than that of PAA, and so it is readily oxidized to chlorine gas, and chlorine gas is known to have a cross sensitivity on the PAA sensor, creating the erratic response.

Compounds that absorb PAA are unsuitable for use in a filter. From testing, examples include iron (III) phosphate, iron (III) oxide removed both hydrogen peroxide and PAA. The two compounds were tested as pure compounds, i.e. not on a solid support, and hematite ($Fe_2O_3$) is known to have a high dielectric constant (dielectric constant=12, CRC Handbook of Chemistry and Physics) and iron (III) phosphate has a similarly high dielectric constant. High dielectric constant materials are known to adsorb PAA (discussed below). Most of the pure compounds tested that were able to remove hydrogen peroxide also removed PAA. Therefore, transition metal catalysts with low dielectric constants (≤~7) can be used as the pure material. However most metal complexes have high dielectric constants and so should be used in small quantities on low dielectric constant solid supports to minimize the adsorption of PAA.

The acid-base properties of the filter are less critical than in some catalytic applications and no special pH control was found necessary. However, the pKa of PAA is 8.2 (https://pubchem.ncbi.nlm.nih.gov/compound/peracetic_acid#section=Top, accessed Mar. 7, 2018), and so very basic catalysts (i.e. pH>~7.5) and supports should be avoided since they are likely to to react with the PAA.

It has been found from testing that filters containing catalysts comprising certain compounds successfully removed hydrogen peroxide vapor and allowed the PAA vapor to pass through essentially unchanged. These compounds included:

Cobalt (II) complexes of EDTA, TEPA, PEHA, acetylacetonate
Copper (II) complexes of EDTA, EN, TEPA, PEHA
Iron (III) complexes of EN, EDTA, TEPA, PEHA, Phen, sulfate
Manganese (II) complexes of EDTA, EN, TEPA, PEHA,
Molybdate salts, such as ammonium molybdate
Nickel (II) complexes of EN, TEPA, PEHA
Palladium complexes of EN, PEHA Where EN=ethylene diamine (metal-ligand ratios 1:1 to 1:4), EDTA=ethylene diaminetetraacetic acid, PEHA=pentaethylenehexamine, Phen=1,10-phenanthroline, TEPA=Tetraethylenepentamine.

These compounds provide examples of filter catalysts. For the purposes of this disclosure, a 'filter catalyst' is a compound which will catalyze the disproportionation of the hydrogen peroxide but be essentially unreactive towards PAA. It may be concluded that amine complexes of the transitions metals (cobalt, copper, nickel, iron, manganese, vanadium, molybdenum, silver, palladium) with chelating ligands, including macrocycles, are effective filter catalysts for the removal of hydrogen peroxide. Similarly, metal complexes with oxygen ligands such as acetylacetonate and mixed amine/oxygen ligands such as EDTA are effective. The compounds listed above are just a few of the many compounds that could be used in this application, based on the selection criteria described above. Those skilled in the art of chemistry will, in light of this disclosure, be able to select metal complexes that will function within the scope of this invention.

The filter catalyst selection criteria above allows the identification of suitable compounds with a degree of confidence. The testing to confirm that the filter catalyst removes essentially all the hydrogen peroxide vapor and allows essentially all the PAA vapor to pass through is simple and quick (minutes) and well within the capabilities of those experienced with the art of gas detection.

A series of candidate filters are prepared as described herein and are tested first as a filter in front of, i.e. in the gas path of a PAA sensor exposed to a test gas containing a known concentration of PAA vapor to determine how much of the PAA will pass through the filter. Secondly, the filter is placed in front of a hydrogen peroxide sensor and exposed to a test gas containing a known concentration of hydrogen peroxide to determine how much of the hydrogen peroxide passes through the filter. The response of the sensors with the filters is compared to the response of the sensor to these respective test gases without a filter. The response of the sensor after 5 minutes is measured and the ratio of the response from the sensor with and without the filter is calculated.

The first test determines whether PAA vapor can pass through the filter and the second whether the filter will remove hydrogen peroxide. A test is deemed successful if the response to PAA vapor, with and without the filter, are of similar magnitude, i.e. essentially all of the PAA vapor has passed through the filter; and the response to hydrogen peroxide on the hydrogen peroxide sensor with the filter is close to zero. This type of testing is routine in developing new gas sensors and is well understood by those experienced in the art of developing gas sensors. The above tests are illustrative and many variations on the above testing may be performed.

If a sample draw system is used, such that the filter is placed in the gas line drawing the gas sample to the sensor, the filter should preferably be designed to minimize the back pressure across the filter for the flow rate of the sensor (typically 0.5 to 1 lpm).

If a diffusion sensor is used, then the filter should preferably be as thin as practical to reduce the impact of inserting an additional diffusion barrier in front of the sensor. The filter should be situated relative to the sensor such that all gas that reaches the sensor must first pass through the filter, and the filter is preferably placed immediately in front of the sensor to avoid any air gaps between the sensor and the filter. Even small air gaps present additional diffusion barriers that can reduce sensitivity.

While the above metal complexes can be used directly in pure form as the catalyst, it is more convenient and effective to use the catalyst on a solid support. The support should be chosen such that it does not significantly react with, absorb or adsorb PAA, has high surface area and has physical and chemical properties amenable for use as a chemical filter employed for use as part of a gas monitor.

Examples of common catalyst supports in the prior art include high surface area pellets, beads and extruded shapes of inert oxides (alumina, silica, zirconia, titania etc), alkali and alkaline earth silicates; porous minerals expanded minerals such as vermiculite; ceramics and molecular sieves; and woven and non-woven fabrics made of inert materials such as inorganic fibers. The primary criterion for selecting a support is:

a) Physical properties such as thickness, particle shape, particle size, texture, fiber or woven/non-woven, porosity, pore size etc. that make it amenable for use in the gas sensor filter. The selection of physical properties for a filter is well known to those experienced in the art of gas detection.

b) Resistance to chemical reaction with PAA. The support should exclude easily oxidizable materials (nylon for example is unsuitable in this application).

c) Resistance to adsorption of PAA. Experimentally, we have found that supports with low polarity, low dielectric constant absorb the least amount of PAA such as the polymers polyethylene, polypropylene and polytetrafluoroethylene. Dielectric constants can refer to the intrinsic property of a material (intrinsic dielectric constant), or the bulk dielectric constant. For a porous material, the bulk dielectric constant may be much less than the intrinsic dielectric constant because it comprises both the intrinsic dielectric constant of the material and the dielectric constant of the air. For purposes of this disclosure, the term dielectric constant refers to the intrinsic dielectric constant. Dielectric constants for many materials have been tabulated, (see for example http://www.clippercontrols.com/pages/Dielectric-Constant-Values.html, accessed Mar. 8, 2018), or they can be easily measured using conventional methods.

Those materials with a very low dielectric constant such as PTFE absorb little PAA but because they are so hydrophobic tend to be more resistant to applying the catalyst to the surface, especially from an aqueous solution. Therefore, a support with low but not very low dielectric support that is moderately hydrophilic and absorbing is preferred, such as Rayon is preferred if the support is being impregnated with the catalyst from an aqueous solution.

The support must also be resistant to oxidation by PAA, otherwise it will remove PAA from the gas stream. Resistant means that there is negligible reaction between the PAA vapor and the support within the time frame that the PAA is in contact with the support. Where the support has a known redox potential, then the support should not be used if it can be oxidized at a potential less than the reduction potential of PAA. However, many do not have reversible reduction potentials. While few compounds have been tested for oxidative stability to PAA, many have been tested for oxidative stability to ozone, and these results have been tabulated (see for example http://www.ozoneapplications.com/info/ozone_compatible_materials.htm and https://www.coleparmer.com/chemical-resistance?PubID=SK&persist=True&ip=no&gclid=EAIaIQobChMI8Ojpitnd2Q-IVlo-zCh0TVwFIEAAYAiAAEgL3_D_BwE, accessed Mar. 8, 2018). Ozone is an even stronger oxidizing agent than PAA, and so if a candidate support material is stable to ozone, it will most likely be stable to oxidation by PAA. Thus the readily available data for ozone compatibility can be used to predict the oxidative stability of materials to PAA.

The general principles for the selection of high surface area supports are well known in the field of catalysts and chemical filters, however the selection criteria depend on the reactions occurring. The conditions needed to make hydrocarbon reformation catalysts are very different than for the formation of ammonia from Nitrogen and hydrogen in the Harber process. It is important to understand which characteristics of the reaction are important. In some reactions it may be the Lewis acidity of the surface, in others the availability of a metal catalytic center with the right stereochemistry. In the present application, the key criteria are to have an inert support that will not react with PAA, but to which the catalyst solvent will wet, so that it spreads out, the surface is such that the catalyst will adhere. The polymers listed work well, as will other materials that meet the criteria listed above.

The methods to prepare these filters are conventional and similar to those used to prepare supported catalysts and other chemicals on high surface area supports. The catalyst may conveniently be deposited on the support by dissolving the active compound in a suitable solvent and apply the solution to the support. The solvent should be selected based on the chemical and solubility properties of the transition metal complex and the support, and for many transition metal compounds, aqueous solution may be used. While there are many possible methods for preparing the filters that will function adequately, the preferred method is to apply an aqueous solution of the metal complex or salt to the support and allow it to air dry at ambient temperature. The most preferred filter was iron (III) ethylenediamine tetraacetic acid complex on a rayon support.

Example

Manufacture of filter for the prevention of hydrogen peroxide vapor from reaching a PAA gas sensor. Iron (III) (EDTA) sodium salt (1 g) was dissolved in water (200 ml). A non-woven sheet of rayon was dipped in the solution, removed, and the excess liquid squeezed out sufficiently to leave the sheet wet but not dripping. The sheet was then placed on a rack to air dry. Once dry, the sheet was cut into disks, similar in diameter to the gas sensors (~3 cm diameter). Two layers of filter disk, comprised the filter which was placed immediately in from of either a sensor responsive to hydrogen peroxide or a sensor that is responsive to PAA. The sensors were then exposed hydrogen peroxide vapor (~10 ppm) or PAA vapor (~2 ppm) in air balance respectively. Compared to the response of the same sensor without the filter, the filter removed over 98% of the hydrogen peroxide vapor, i.e. substantially all of the hydrogen peroxide and allowed over 80% of the PAA to reach the sensor. In this example, the sensors were operating in diffusion mode, not sample draw.

The above filters also gave a response to PAA that was over 80% of the response without the filter. A reduction in signal will be a combination of the added diffusion barrier caused by the addition of the filter as well as any losses of PAA due to adsorption or reaction with the filter. Some of the <20% decrease in signal will be due to the added diffusion barrier presented by the filter, so the loss due to reaction with PAA or adsorption of PAA is small.

In the preferred embodiment, the filter is built into a gas detection instrument containing the PAA sensor and the instrument is calibrated with a known concentration of PAA vapor, so that the gas detection instrument displays directly the concentration of PAA. Any small reductions in the amount of PAA reaching the sensor is thus compensated for by the calibration.

The filters described herein comprising a hydrogen peroxide disproportionation catalyst also demonstrated significantly larger capacity to hydrogen peroxide than filters made with simple oxidizing agents (such as cerium (IV) salts) and even after the hydrogen peroxide had started to break through the filters after applying very high concentrations of hydrogen peroxide (>10 ppm) for prolonged periods and continued to keep the amount of hydrogen peroxide vapor reaching the sensor well below the concentration absent the filters. It is believed that these filter compounds function through disproportionation of the hydrogen peroxide and so the active agent is a catalyst rather than a consumed reagent. This explanation is consistent with the longer life of the filter and the continued removal of the hydrogen peroxide even when faced with prolonged exposure to high concentrations of hydrogen peroxide.

These filters can be used with any type of gas sensor used to detect PAA in the potential presence of hydrogen peroxides. The filters may be placed on the outside of the sensor or they may be incorporated within the sensor at manufacture. The key positional requirement is that the filter must be in the gas path (the path the gas must pass to travel from ambient air into the sensor where it is detected), thus any gas which is going to enter the sensor must pass through the filter. For sample draw devices, i.e. gas monitors who draw is a sample of gas from the target location via a tube, using a pump, the filter can be placed in-line, such that all the gas passes through the filter before reaching the sensor.

Similarly, the filter materials described above can be used in other applications where it is desirable to allow the passage of PAA into a device but not hydrogen peroxide. For example, this filter may be used to generate a PAA test gas free of hydrogen peroxide or make a gas detector tube that responds to oxidizing agents specific to PAA in the presence of hydrogen peroxide. For example, a common detector tube for hydrogen peroxide responds to both hydrogen peroxide and PAA. By installing one of these filters upstream of the detecting reagent, the gas detection tube can be made specific to PAA. For purposes of this disclosure, the term detector includes any means for detecting PAA, including sensors for PAA, including electrochemical, photoacoustic, impingers, gas detection tubes, infrared and visible photometers, thermal sensor, exposure badges There are many chemical assays that detect both PAA and hydrogen peroxide and the response of the assay without the present invention will provide a measure of the PAA and the hydrogen peroxide, whereas an assay with the present invention will provide only the PAA. Combining these results gives independent values for both the hydrogen peroxide and the PAA.

The filter may be used with sensors for PAA vapor. The principle sensor used today to measure PAA vapor is an electrochemical sensor (e.g. PAA monitor from ChemDAQ Inc, Pittsburgh, Pa.), but other types of sensor may also be used.

Typically, the vapor being analyzed reaches the sensor either by diffusion in which case the sensor is located at the point to be measured, or the air is drawn in from the sample point by means of a pump and delivered to the sensor for analysis, a so-called sample draw system. If a diffusion type sensor is employed, then the filter should be placed in the gas path immediately in-front of the sensor such that all the gas diffusing to the sensor must first pass through the filter. The filter can thus be a separate component from the sensor in the gas monitor, or the filter can be incorporated into the sensor, such that the sensor and filter comprise a single unit. Other types of chemical filters have been incorporated into electrochemical sensors in the prior art, for example the 7E/F carbon monoxide sensor and 7ST/F sulfur dioxide sensor from City Technology Ltd, Portsmouth, United Kingdom, both have integrated filters.

The filter may be used in a fixed gas detection monitor, also known as an area monitor, or it may be used in a portable monitor, such as is used to provide personal monitoring. i.e. determining the exposure that an individual has received to PAA vapor. Both types of monitor are widely used for occupational safety to ensure that workers in a work environment are not exposed to PAA vapor over occupational exposure limits.

The filter of the present invention offers significant advantages over conventional chemical filters. The amount of gas which is required to flow through the filter will depend on the instrument design, but the size of the filter and the capacity of the filter will have to be selected to meet the expected demand for interferent gas removal over the life of the filter. For a conventional filter, to achieve a large capacity, the filter must be large enough to contain sufficient filter medium to reach that capacity goal. A larger filter will result in a greater diffusion barrier, lower sensitivity and longer response times. By using a disproportionation catalyst filter as in the present invention, the filter is not consumed during the filtering reaction and so the filter size can be much smaller (lower diffusion barrier) since it is based on the minimum filter needed to remove the hydrogen peroxide rather than the capacity of the filter. Therefore the filter can be much smaller, the sensor sensitivity greater (better signal to noise) and the response time faster.

A typical application of the present invention is shown in FIG. 1. A gas detection instrument 10 for PAA incorporates a sensor 11 for PAA that operates in diffusion mode. Both the sensor 11 and the instrument 10 are conventional. The sensor 11 may for example be an electrochemical sensor. PAA vapor would normally enter the sensor as part of the detection process via aperture 12 by natural diffusion. The sensor 11 would detect the PAA within the gas and provide a suitable electronic signal to the instrument 10. To prevent interferent gases from reaching the sensor 11 and causing false signals, a filter 14 is placed in the gas path to sensor 11. This filter 14 contains a filter medium 15 that selectively reacts with hydrogen peroxide vapor but allows the PAA vapor to pass. The filter 14 is placed over the aperture 12 of the sensor 11 such that all the PAA containing gas entering the sensor must pass into the filter 14 through an opening 13, pass through the filter medium 15 before it can enter the sensor 11 via the aperture 12. The filter 14 may for example be constructed of plastic (e.g. polyethylene, ABS etc.) or other materials that provide a means to keep the filter material 15 in the gas path in front of the sensor aperture 12 and provides means for the gas to enter the filter enclosure via a suitable opening 13 comprised of, for example, sintered plastic. The design of the filter enclosure is simple and conventional for anyone experienced in the art of mechanical design and construction pertaining to electrochemical gas sensors and many configurations are known in the prior art.

Figure 2:
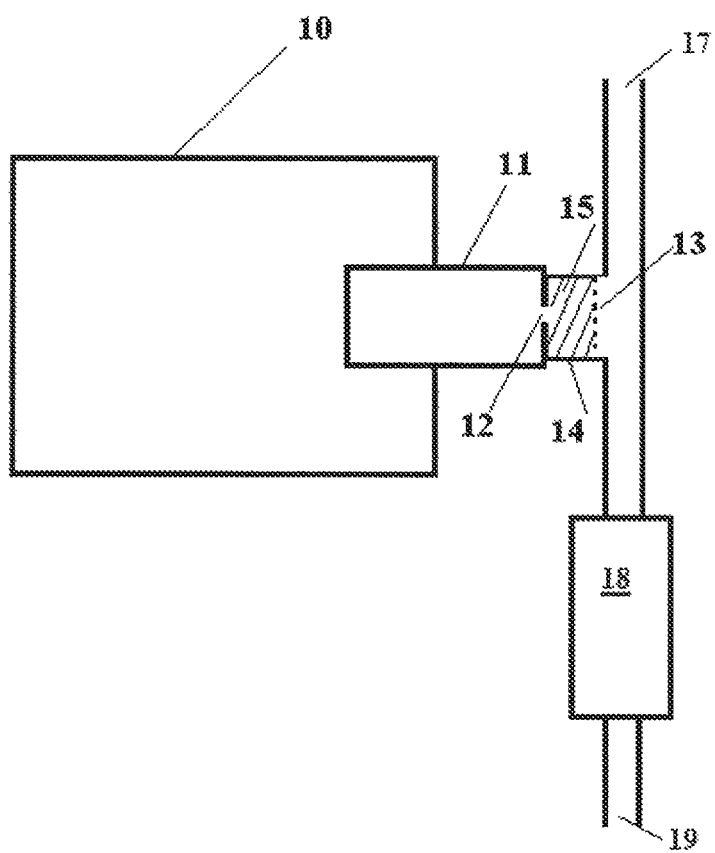
FIG. 2 is a diagram of sensor operating in sample draw mode with the filter in the gas path prior to the sensor.
Figure 3:
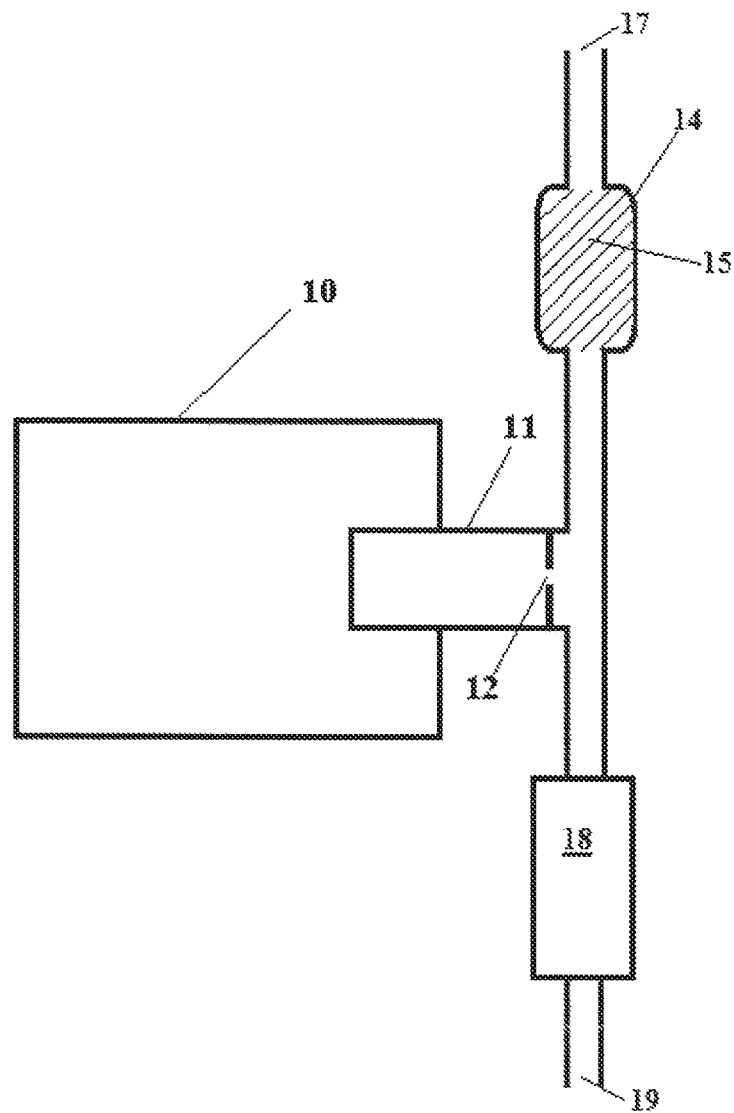
FIG. 3 is a diagram of a sensor operating in sample draw mode with the filter in-line with the pump.

FIG. 2 and FIG. 3 show the sensor being operated in sample-draw mode. In FIG. 2, the gas is in drawn in through opening 17 by pump 18 and expelled via exit 19. The gas flows past the filter 14, such that some of the gas can enter filter 14 via filter opening 13 and diffuse through the filter to the sensor 11. The other labels have the same meaning as in FIG. 1.

FIG. 3 is similar to FIG. 2, except that the filter 14 is placed in line with the gas stream entering via opening 17, passing through the filter 14 containing filter medium 15, passed the opening to the sensor 12, such that some of the gas can diffuse into sensor 11. The rest of the gas stream is drawn by the pump 18 and expelled via the exit 19.

While the preferred embodiments of the invention have been shown and described, it will be apparent to those skilled in the art that changes can be made in the embodiments without departing from the spirit and principles of the invention.

I claim:

1. A peracetic acid detection system comprising a detector sensitive to peracetic acid vapors and a filter positioned in relation to the detector within the gas path with respect to the detector, such that gas reaching the detector first passes through the filter, the filter reducing the cross sensitivity of the detection system to hydrogen peroxide vapor, by chemically reacting with essentially all of any hydrogen peroxide vapor that is present in the gas but not chemically reacting with the peracetic acid vapor in the gas, thus allowing the peracetic acid vapor to pass through the filter to the detector; wherein the filter comprises a filter catalyst comprising a transition metal complex in its highest stable oxidation state, wherein the complex is firstly capable of catalyzing the disproportionation of hydrogen peroxide, said capability being determined by the first reduction potential of the said complex occurring both at an electrochemical potential positive of the oxidation of hydrogen peroxide and negative of the reduction of hydrogen peroxide; and the complex (including the metal, ligands and any counter ions) is secondly further inert towards oxidation by peracetic acid.

2. The peracetic acid detection system of claim 1, wherein the detector is selected from the group consisting of an electrochemical gas sensor, a gas sensor, an impinger containing a solution for collection of peracetic acid, an exposure badge, a gas sample collection tube, of and a colorimetric gas detection tube.

3. The peracetic acid detection system of claim 1 wherein the filter catalyst is deposited on a solid support with a dielectric constant of less than 5; and said solid support is resistant to oxidation by peracetic acid.

4. The peracetic acid detection system of claim 3 wherein the solid support is selected from the group consisting of ceramics, glasses, rayon, cellulose paper, organic polymers, and hydrocarbon polymers.

5. The peracetic acid detection system of claim 1 wherein the filter catalyst is selected from the group consisting of the following transition metal complexes Cu(EDTA), Cu(EN)$_2^{2+}$, Cu(II)(TEPA)$^{2+}$, Cu(PEHA)$^{2+}$, Fe(III)(EN)$_3^{3+}$, Fe(III)(EDTA)$^-$, Fe(III)(TEPA)$^{2+}$, Fe(III)(PEHA)$^{2+}$, Fe(III)(Phen)$_2^{2+}$, Fe$_2$(SO$^4$)$^3$, (NH$_4$)$_2$(MoO$_4$), Ni(II)(EN)$_3^{2+}$, Ni(II)(TEPA)$^{2+}$, Ni(II)(PEHA)$^{2+}$, Pd(III)(EN)$_3^{2+}$, Pd(PEHA)$^{2+}$.

6. The peracetic acid detection system of claim 1 wherein the filter catalyst is the iron (III) complex of ethylenediaminetetraacetic acid and said filter catalyst is on a rayon support.

7. A peracetic acid monitor comprising a sensor sensitive to peracetic acid vapors and a filter positioned in relation to the sensor within the gas path with respect to the sensor, such that gas reaching the sensor first passes through the filter, the filter removing any hydrogen peroxide vapor that is present in the gas by chemical reaction, wherein the filter does not chemically react with any peracetic acid vapor present in the gas, thus allowing the peracetic acid vapor to pass through the filter to the sensor; the filter containing a transition metal filter catalyst in its highest stable oxidation state which is capable of catalyzing the disproportionation of hydrogen peroxide, the filter catalyst being deposited on a solid support, and wherein the solid support is unreactive to oxidation by peracetic acid.

8. The peracetic acid monitor of claim 7 wherein the solid support is selected from the group consisting of alkali and alkaline earth silicates, glass fiber paper, rayon, cellulose paper, silica fibers, and vermiculite.

9. The peracetic acid monitor of claim 7, wherein the solid support has a morphology selected from the group consisting of powders, porous membrane, fibers, pellets, beads, woven cloth, non-woven cloth or extruded shapes and expanded minerals.

10. The peracetic acid monitor of claim 7 wherein the gas entering the sensor passes through the filter by diffusion.

11. The peracetic acid monitor of claim 7, wherein the gas is delivered to the sensor by means of a pump.

12. The peracetic acid monitor of claim 7 wherein the filter is placed in a stream of flowing gas being drawn by a pump.

13. The peracetic acid monitor of claim 7, wherein the filter is placed within the sensor.

14. The peracetic acid monitor of claim 7, wherein the filter is incorporated into the gas path of the sensor at the time of manufacture of the sensor.

15. The peracetic acid monitor of claim 7, where the sensor is an electrochemical gas sensor for peracetic acid vapor.

16. The peracetic acid monitor of claim 7, wherein the monitor is a portable gas monitor.

17. The peracetic acid monitor of claim 7, wherein the monitor is a fixed gas monitoring system.

18. A peracetic acid detector comprising a sensor sensitive to peracetic acid vapor and a filter positioned in relation to the sensor within the gas path with respect to the sensor, such that gas reaching the sensor first passes through the filter, the filter chemically reacting with hydrogen peroxide vapor within the gas, thereby preventing the hydrogen peroxide vapor from reaching the sensor, said the filter comprising the iron (III) complex of ethylenediaminetetraacetic acid on a rayon support.

19. The peracetic acid detector of claim 18, wherein the detector is an electrochemical gas sensor.

* * * * *